United States Patent [19]

Poncy

[11] Patent Number: 4,816,022
[45] Date of Patent: Mar. 28, 1989

[54] HYPODERMIC SYRINGE WITH SLIDING CAP

[76] Inventor: George W. Poncy, 3725 Investment La., Riviera Beach, Fla. 33404

[21] Appl. No.: 129,188

[22] Filed: Dec. 7, 1987

[51] Int. Cl.[4] .............................................. A61M 5/32
[52] U.S. Cl. ..................................... 604/198; 604/263
[58] Field of Search ................ 604/198, 187, 192, 263

[56] References Cited

U.S. PATENT DOCUMENTS

| | | | |
|---|---|---|---|
| 4,631,057 | 12/1986 | Mitchell | 604/198 |
| 4,695,274 | 9/1987 | Fox | 604/198 |
| 4,772,272 | 9/1988 | McFarland | 604/263 X |

Primary Examiner—John D. Yasko
Attorney, Agent, or Firm—Lane and Aitken

[57] ABSTRACT

In a hypodermic syringe having a sliding cap to prevent accidental pricking of the user, a needle hub assembly is provided with radial flaps having arcuate bands which extend in both circumferential directions from the ends of the radial flaps. The arcuate bands make a sliding engagement with the interior surface of the cap. An interference bead is positioned on the interior surface of the cap so that when the arcuate bands are positioned between the interference bead and the mouth of the cap and in engagement with the interference bead, the proximal end of the needle hub assembly will be spaced from the mouth of the cap within the cap.

6 Claims, 2 Drawing Sheets

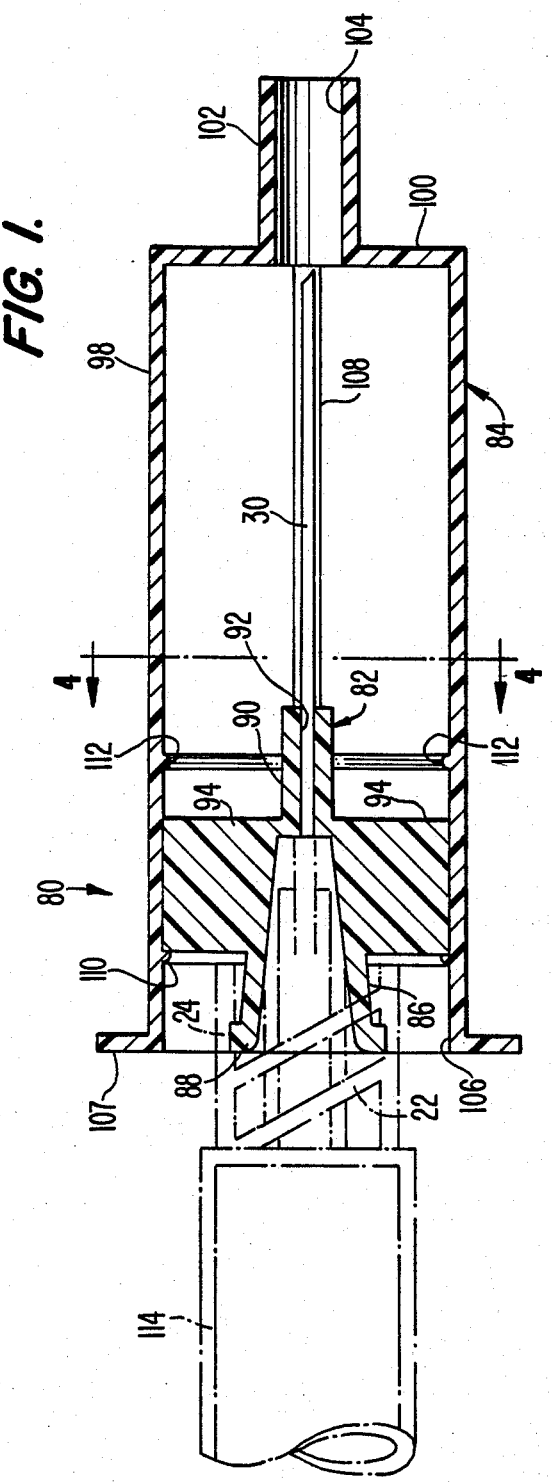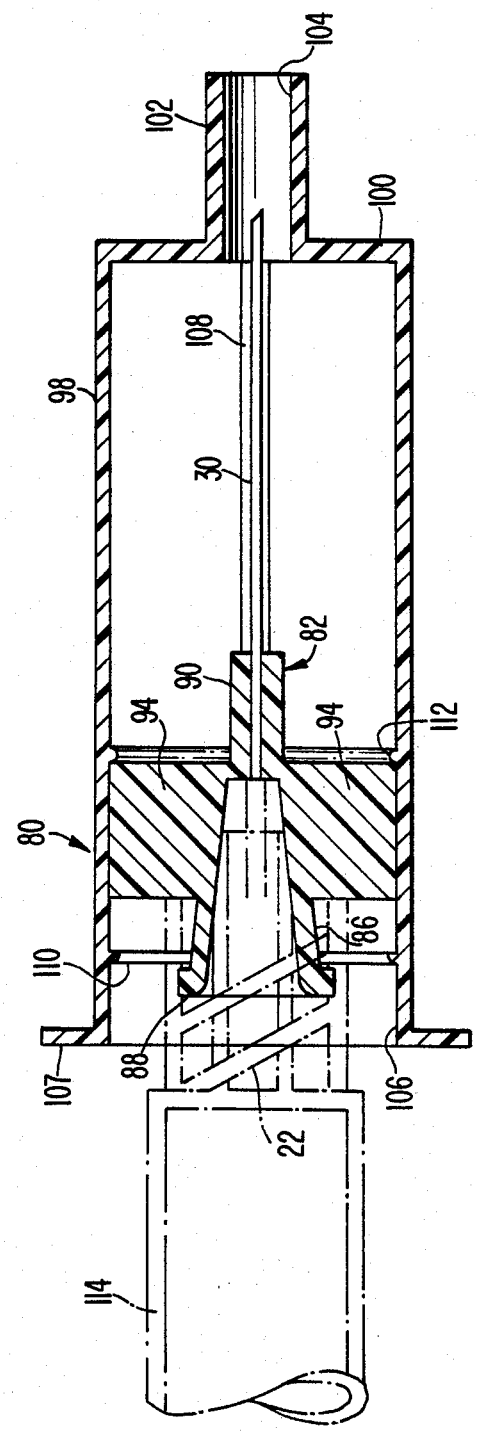

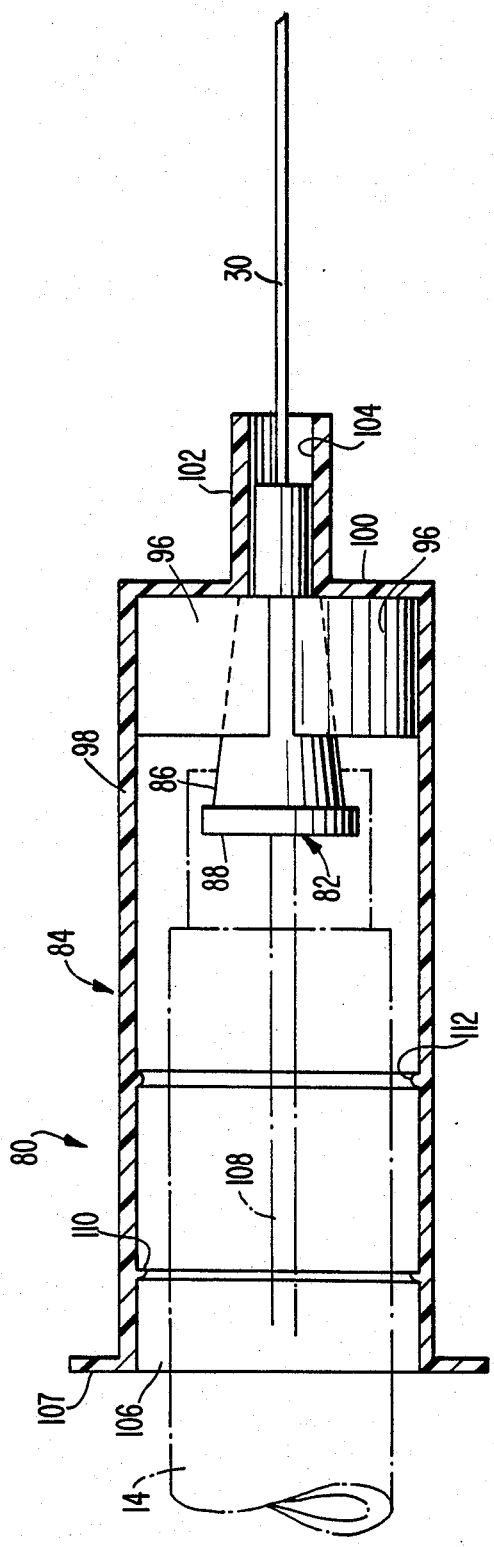
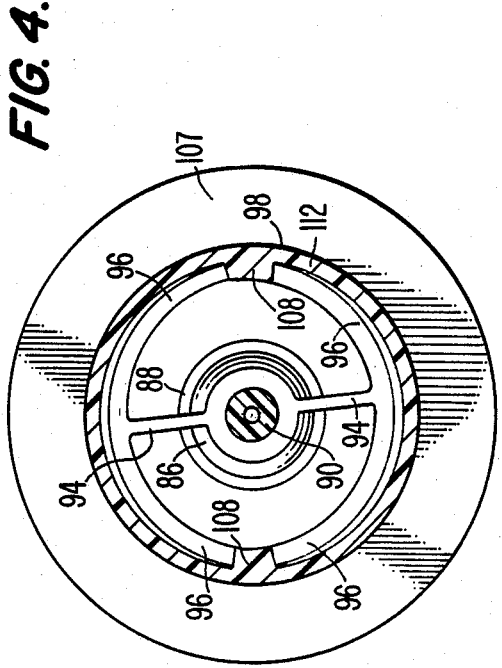

HYPODERMIC SYRINGE WITH SLIDING CAP

BACKGROUND OF THE INVENTION

This invention relates to hypodermic syringes for withdrawing blood or infusing a patient with serums and the like and, more particularly, to a hypodermic syringe designed to prevent accidental pricking of the fingers or hands of the person using the syringe.

With conventional hypodermic syringes, the administration of an injection or blood withdrawal involves the removal of a protective cap covering the needle of the syringe and, after the withdrawal of the needle from the body of a patient, the replacement of the cap over the needle before the needle is discarded. The procedures just-described can easily lead to the accidental pricking of a hand or finger of the administrant, the injection of harmful viruses and bacteria under the skin, and the resultant infection of the administrant. In view of the increasing occurrence of fatal diseases such as Acquired Immune Deficiency Syndrome (AIDS), it is absolutely essential that accidental needle pricks be avoided.

Accidental pricking occurs most often during the removal and replacing of the needle cap. It is at these moments that the hand of the administrant is nearest to the sharp needle point. More specifically, the most common accidental pricking occurs because the cap is firmly held in place over the needle by friction between the cap and a hub in which the needle is mounted. A large frictional force is intentionally provided, such as by the engagement of ribs formed on an external surface of the needle hub and on an internal surface of the cap, so that the cap does not inadvertently become dislodged from the needle and, thereby, cause the previously sterile needle to become contaminated. In order to overcome the frictional resistance, the administrant must firmly grasp the cap and pull. The release of the cap from the needle hub occurs suddenly, so that there is a tendency for the hand to whip back towards the exposed needle, causing an accidental prick to occur. Accidental pricking also occurs when the cap is being replaced over the needle, since the opening in the cap into which the needle must be inserted is quite small. As a result, a slight misjudgment or unsteadiness causes the needle, instead of entering the small cap opening, to miss the opening and prick the finger of the administrant, which, by virtue of holding the cap, must of necessity be near the cap opening. In fact, such accidental pricking occurs even though caps of excessive length are used to cover even a short needle in an effort to increase the distance between the needle and the administrant's hand. For example, a cap used to cover a 1-½ inch long needle may be as much as 2 inches long.

Copending application Ser. No. 73,682, filed by the applicant of this invention on July 15, 1987 describes a hypodermic needle assembly which overcomes the problems of accidental pricking in the removal and replacement of the needle caps. In the assembly of the application, a cap is incorporated as an integral part of the hypodermic unit, so that the cap requires no removal or replacement. The cap is slidably mounted on formations projecting from a hub in which the needle is mounted. The projecting formations include flaps projecting radially from the hub and resilient bands extending arcuately in one direction from the flaps to contact and guide the cap, maintaining the longitudinal axis of the cap in substantial alignment with the longitudinal axis of a syringe needle. As a result, any danger of the needle piercing a sidewall of the cap, especially during the sliding of the cap, is avoided. The cap has a diameter larger than the diameter of the syringe and a proximal end which is open to permit the cap to move down over the syringe and slide on the arcuate resilient bands. An opposite end of the cap is closed in the sense that there is no opening large enough for a finger to enter and come into contact with the needle. There is, however, an opening large enough for the needle to pass through to reach an exposed position in which an injection or withdrawal can be administered.

In one embodiment disclosed in the copending application, the cap is retained in the extended position by the engagement of the resilient bands with an annular interference bead on the inner surface of the cap, spaced from the proximal end of the cap, and the separation of the cap from the needle and the needle hub is prevented by the engagement of the resilient bands with an annular stop bead on the inner surface of the cap adjacent the proximal end. In addition, elongate axial ribs on the interior surface of the cap are received in gaps provided between the flaps and adjacent free ends of the arcuate resilient bands. Rotation of the cap causes the elongate ribs to push the bands and, thereby, rotate the needle hub to screw it onto the barrel of the syringe.

SUMMARY OF THE INVENTION

The present invention is an improvement in the above described embodiment to reduce the chances of the cap being accidentally slid to a position to expose the needle and also to facilitate molding the needle hub to provide a more uniform frictional force between the resilient bands and the interior wall of the cap.

In accordance with the present invention, the annular stop bead on the inner surface of the cap, instead of being adjacent to the proximal end of the cap, is spaced inwardly from the proximal end so that when the cap is positioned on the needle hub with the resilient bands in engagement with the stop bead, the lower end of the needle hub will be approximately aligned with the lower end of the cap. The interference bead on the inner surface of the cap is spaced inwardly from the stop bead by an amount substantially larger than the axial dimension of the resilient bands. When the cap is positioned on the needle hub with the resilient bands positioned between the stop bead and the interference bead and in engagement with the interference bead, the cap will cover the needle and the lower end of the needle hub will be spaced from the lower end of the cap within the cap. This structure reduces the chances of something coming in contact with the needle hub and pushing it accidentally further into the cap so that the resilient bands are pushed partially past the interference bead. While such accidental pushing of the needle hub within the cap would probably not expose the needle, there is a chance that the needle would become accidentally prematurely exposed when the needle hub and cap assembly is screwed onto a syringe body and possibly prick the user. By having the interference bead located so that the bottom of the needle hub is within the cap when the interference bands are in engagement with an interference bead, the chances of the resilient bands being accidentally pushed past the interference bead prematurely is substantially eliminated. The stop bead is located spaced within the cap rather than at the proximal end of the cap so that the bands only need to be slid a small distance between the position where the bands engage the stop bead and the position and which the bands engage the interference bead. It is preferable for this distance to be a relatively small distance to increase the control of the user when he is mounting the needle and cap assembly on a syringe body and reduce the chances that in the mounting of the needle and cap assembly on the syringe body, the user will accidentally push the cap too far onto the needle hub to expose the needle prematurely.

In addition, in the present invention, instead of having a single resilient band extending from each flap in one direction a little less than 180 degrees, two resilient bands extend in both circumferential directions from each flap to a little less than 90 degrees wherein four resilient bands are provided instead of two and the resilient bands are considerably shorter. This arrangement overcomes a problem in molding the band structure of the copending application so that the needle hub and cap assembly has the same operating characteristics in each manufactured unit. The neutral position of the resilient bands in the final molded depends upon the parameters of the molding process which are difficult to control. As a result, there tends to be a variation in the amount that the bands are flexed from their neutral position when the bands are inserted in the cap. Accordingly, the frictional force with which the resilient bands engage the interior wall of the cap varies. When the bands extend over almost 180 degrees as described in the above-mentioned copending application, this effect is magnified. By reducing the length of the bands to a little less than 90 degrees as disclosed in the present application, the frictional force with which the bands engage the cap is made more nearly uniform from unit to unit, and as a result, the amount of force required to slide the cap on the needle hub assembly is made more nearly uniform in different manufactured units.

BRIEF DESCRIPTION OF THE DRAWINGS

FIG. 1 is an axial sectional view of the hypodermic syringe assembly of the present invention.

FIG. 2 is an axial sectional view of the syringe assembly shown in FIG. 1 with the cap of the assembly partially retracted.

FIG. 3 is an axial sectional view and partial elevation of the syringe assembly of FIG. 1 with the assembly rotated 90 degrees relative to FIG. 1 and with the cap in a fully retracted position exposing the needle.

FIG. 4 is a cross-sectional view taken along the line 4—4 in FIG. 1.

DETAILED DESCRIPTION OF THE PREFERRED EMBODIMENT

As shown in the drawings, the assembly of the invention which is designated generally by the reference numeral 80, comprises a needle portion 82, and a closure or cap portion 84 enclosing the needle portion 82. The needle portion 82 includes a hollow conical needle hub 86 with a rim 88 for connecting with the male threads 22 of a syringe body 14 in a Luer lock. A cylindrical post 90 on the needle hub 86 has a bore 92 for receiving a needle 30. Two flaps 94 project radially from the needle hub 86, and arcuate resilient bands 96 extend in each direction from the radially outer end of each flap 94 to free ends spaced by a gap from an adjacent band 96. A gap of 16 degrees, for example, has been found to be appropriate. The bands 96 are integral with the flaps 94 and have a radius at their free ends are slightly greater than the radius of the internal surface of a generally cylindrical cap body 98 in their unflexed state, that is before they are inserted in the cap body 98. The areas of intersection of the bands 96 and the flaps 94 act as spring-loaded hinges to bias the bands 96 against the cap body 98, whereby the cap body can reciprocate by sliding on the bands without substantial wobble, thereby maintaining the longitudinal axis of the cap body 98 substantially aligned with the longitudinal axis of the needle 30.

Because the circumferential length of the bands 96 is only about 82 degrees instead of 172 degrees as disclosed in the copending application, there will be less variation in the radial dimension of the bands 96 at their free ends in their unflexed state due to variations in the molding process. As a result, there will be less variation in the frictional force applied by the bands 96 to the inner cylindrical wall of the cap body 98. Accordingly, the force required to reciprocate the cap body 98 on the bands is more uniform from unit to unit.

The cap body 98 is slightly tapered, for example, a taper of 2 degrees, from its end proximal to the syringe body 14 to its end distal from the syringe body, and the arcuate resilient bands 96 may be tapered in the same sense. In this way, the cap portion 84 is retained in a retracted position exposing the needle 30. The cap body 98 has a shoulder 100, a hollow cylindrical cap extension 102, a reduced-diameter opening 104, and a large opening 106. In addition, the cap body 98 includes an exterior annular flange 107 at its proximal end.

As can be seen from FIG. 4, when viewed together with FIGS. 1 and 3, two elongate axial anti-twist ribs 108 are defined on the interior of the cap body 98. The ribs 108 project into the gaps between the free ends of the bands 96, thereby permitting reciprocation of the cap body 98 relative to the needle portion 82 while preventing rotation of the cap body relative to the needle portion. Therefore, the needle portion 82 can be screwed onto the syringe body 14 by rotating the cap body 98. In addition, the width of the ribs 108 is made slightly larger than the width of the gaps between the bands 96, for example, 16.5 degrees compared to 16 degrees, to force the free ends of the bands 96 away from the adjacent flaps 94 and against the cap body 98 in a pivoting action around a pivot axis through the intersection of the arcuate resilient bands 96 and their integral flaps 94. The ribs 108 can be made even wider to provide a tighter fit between the arcuate resilient bands 96 and the cap body 98.

The cap body 98 is retained on the needle portion 82 by the engagement of the arcuate resilient bands 96 with an annular stop bead 110 on the inner surface of the cap body 98 spaced from the large opening 106 at its proximal end. The stop bead 110 has the crosssection of a 90 degree sector of a circle with a flat surface facing toward the distal end of the cap portion 84. The stop bead 110 is spaced from the large opening 106 of the cap body 98 by an amount such that when the needle portion is inside the cap with the bands 96 in engagement with the inner side of the stop bead, the bottom of the rim 88 will be aligned approximately with the bottom of the annularly flange 107 of the cap body as shown in FIG. 1. The cap body 98 also includes on its inner surface an annular interference bead 112 spaced from the stop bead 110 by a distance substantially greater than the axial dimension of the bands 96. As a result, when the bands 96 are between the stop bead 110 and the interference bead 112 and in engagement at their upper ends with the interference bead as shown in FIG. 2, the bottom of the needle hub 36, that is the bottom surface of the rim 88, will be well within the cap body 98. With this arrangement, it is unlikely that a force will be accidentally applied to the bottom of the needle hub 86 and cause it to be pushed inwardly so that the bands 96 are started past the interference bead 112 before the needle hub and cap assembly are connected with a syringe body. The reason that the distance between the stop bead 110 and the interference bead 112 is greater than the axial dimension of the bands 96 is to make it easier for someone assembling the needle portion 82 into the cap portion 84 to stop the momentum of the needle portion 82 after the needle portion pops past the stop bead 110. The stop bead could be located adjacent the large opening of the cap body 98, but its preferably located spaced inside the cap body to reduce the distance that the bands 96 can be reciprocated between the stop bead 110 and the interference bead 112. This reduced distance provides for increased control by the user when he attaches the needle portion on a syringe body by screwing the hub 86 onto the Leuer Lock threads 22 of the syringe body. This added control is important so that the needle portion and cap portion can be screwed into the Leuer Lock threads 22 without prematurely pushing the bands 96 past the interference bead 22 and exposing the needle during the assembly.

After the needle portion and cap portion have been assembled on a syringe body, the needle can be exposed by sliding the cap portion 94 on the bands 96 so that the bands 96 slide over the interference bead to the position illustrated in FIG. 3 wherein the bands 96 and flaps 94 engage the shoulder 100 of the cap body, whereupon the needle will be exposed.

After the syringe has been used for an injection or drawing blood, the needle is recovered simply by sliding the cap portion back up over the needle so that the bands 96 are again between the stop bead 110 and the interference bead 112.

The above description is of a preferred embodiment of the invention and modification may be made thereto without departing from the spirit and scope of the invention, which is defined in the appended claims.

What is claimed is:

1. A needle and cap assembly for attaching to a hypodermic syringe body comprising a needle, a hub mounting said needle, and having means to mount said hub on a syringe body, a cap slideably mounted on said hub between a first position in which said cap covers said needle and a second position in which said cap exposes said needle, said hub having bands making a sliding fit with an interior surface of said cap, said cap having a mouth at one end and an interference bead on the interior surface of said cap spaced from said mouth, said bands being located between said interference bead and said mouth and in engagement with said interference bead when said cap is in said first position, the bottom end of said hub opposite said needle being entirely within said cap spaced from said mouth when said cap is in said first position, said interference bead and said bands comprising means to provide an increased resistance to said cap sliding further onto said hub toward said second position from said first position.

2. A needle and cap assembly as recited in claim 1, wherein a stop bead is provided on the interior surface of said cap between said bands and said mouth when said cap is in said first position, said stop bead and said bands comprising means to prevent said cap from being removed from said hub.

3. A needle and cap assembly as recited in claim 2, wherein said stop bead is spaced from said mouth within said cap.

4. A needle and cap assembly for attaching to a hypodermic syringe body comprising a needle, a hub mounting said needle, and having means to mount said hub on a syringe body, a cap slideably mounted on said hub between a first position in which said cap covers said needle and a second position in which said cap exposes needle, said cap having a plurality of radially extending flaps mounted thereon and bands mounted on the outer end of said flaps, said bands extending circumferentially in both directions from said flaps, said bands making a sliding fit with an interior surface of said cap.

5. A needle and cap assembly as recited in claim 4, wherein said flaps consist of two flaps mounted in diametrically opposite sides of said hub.

6. A needle and cap assembly as recited in claim 4, wherein said bands define gaps between adjacent ones of said bands extending from different flaps, said cap having axially extending ribs on the interior surface of said bands located within said gaps.

* * * * *